Nov. 26, 1963 J. L. MOSSHOLDER ETAL Plant Pat. 2,315
AZALEA PLANT
Filed May 28, 1962
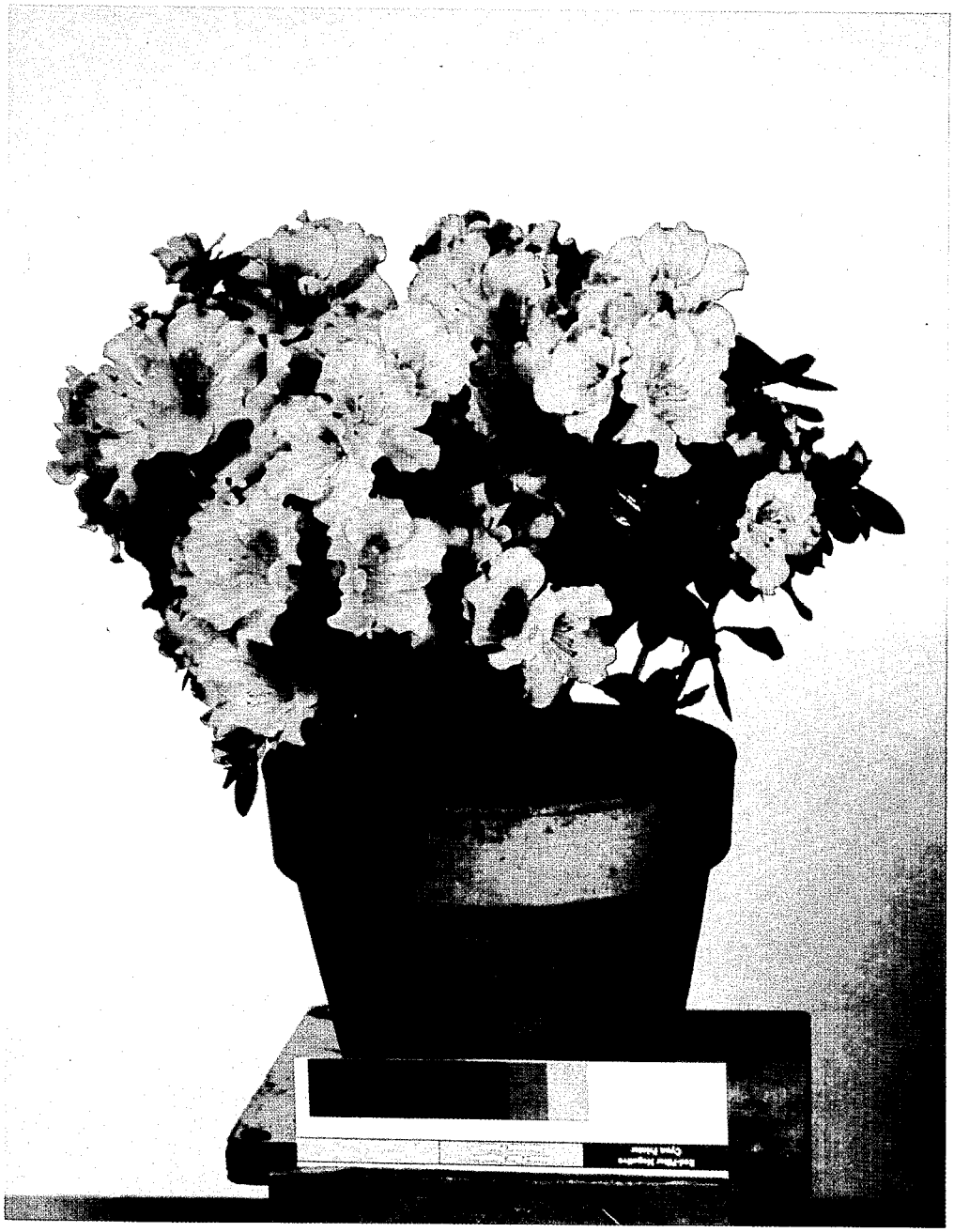

United States Patent Office

Plant Pat. 2,315
Patented Nov. 26, 1963

2,315
AZALEA PLANT

Joseph Lynn Mossholder, Costa Mesa, and Milford W. Portwood, San Clemente, Calif., assignors to Gold Cup Azaleas, San Clemente, Calif., a partnership Filed May 28, 1962, Ser. No. 198,385
1 Claim. (Cl. Plt.—57)

This invention relates to a distinct and new variety of azalea plant.

This new variety of azalea plant has been obtained as a result of deliberate hybridization experiments carried out in Orange County, California, involving the cross-breeding of an unpatented seedling designated by the number K–16 female parent azalea and an unpatented "Dr. Bergman" male patent azalea, and has been given the number X–5 for identification purposes.

This new variety of azalea plant has been asexually reproduced in Orange County, California, from its own cuttings a sufficient number of times so as to clearly show that the various characteristics of this plant as set forth in this specification are permanently fixed. The accompanying illustration of a forced cutting of the azalea plant of this invention in bloom shows the prolific blooming and striking deep red color of the flowers of this plant.

When the new "Red Cap" azalea of this invention is grown and properly pinched in accordance with conventional practice it has an exceptionally long season when it can be forced. This season is from October to March. This new plant is a compact grower having dependable, consistent and heavy bud-setting qualities. The flowers porduced by it are of a deep red color, and the holding quality of these flowers is excellent. As a consequence of these characteristics the new azalea of this invention is considered to be an excellent plant for florists.

The various characteristics of this azalea plant and flowers are described specifically and in detail in the following:

*Plant*

Form of plant: Bushy; symmetrical.
Growth habit: Fast compact grower.
Rooting: Roots well with vigorous roots, grows strongly on its own roots.
Blooming habit: Prolific bloomer; holds original color well throughout the blooming period; flowers hold well.
Blooming season: The outdoor heavy blooming season in southern California is in March. This variety can be forced into bloom in a glasshouse by Thanksgiving Day by proper pinching or any date thereafter until March. The flowers bloom evenly when forced.
Suitability for forcing: Excellent.

*Foliage*

Size: Mature leaves average 1" wide by 2" long.
Quantity: Abundant.
Color: New foliage—light green top and bottom. Old folige—dark green and glossy on upper side; underside, lighter green and dull.
Shape: Oval and slightly pointed on end.
Texture: Normal on both upper and under side.
Edge or margin: Normal.
Ribs and veins: Recessed on upper surface and protruding on lower surface.
Aspect: Considerably darker than average azalea foliage.

*Flower*

Size: 2 to 2½" average across.
Flower borne: Usually two on a stem.
Quantity of bloom: Abundant.
Form: hose in hose, with the outside layer of petals much smaller than inside layer.
Continuity: Long lasting flowers and holds original color exceptionally well; good forcing variety.
Petalage: (*a*) *Size.*—1" to 1¼" wide and 1½" long.
(*b*) *Number of petals under normal condition.*—Two layers of petals; five petals on inside of hose or cycle of petals; five to ten petals and petaloids on outside hose or cycle of petals. Occasionally, the flowers form petaloids in center of flower.
(*c*) *Color of bud.*—Plate #385 Plochere color system.
(*d*) *Color of open flower.*—Plate #385 Plochere color system; upper ⅓ of flower is speckled and blotched with much darker shades of Plate #385 Plochere color system.
(*e*) *Texture.*—Smooth.
(*f*) *Appearance.*—Abundant wide open flowers of dark red with slightly ruffled edge. There is depth in the throat, making it a trumpet shaped flower.

*Reproductive Organs*

Stamens: Usually 6 to 8 each flower except when petaloids appear; in which case, the number of stamens is reduced.
(*a*) *Anther.*—Normal.
(*b*) *Filament.*—Normal; same color as specks in throat of flower.
Pollen: Pale yellow.
Style: Plate #385 Plochere color system.
Stigma: Plate 385 Plochere color system.
Ovary: Normal.

Having illustrated and described the invention or discovery what is claimed as new and patentable is:

A distinct and new variety of azalea plant, substantially as illustrated and described as hereinabove and characterized generlly by its unusual qualities of heavy, dependable bud-setting, the deep red color of its flowers, its fast bushy growth, its long forcing season and its holding of flowers after being forced.

No references cited.